United States Patent
Barger et al.

(10) Patent No.: US 9,162,955 B2
(45) Date of Patent: *Oct. 20, 2015

(54) PROCESS FOR PYROLYSIS OF A COAL FEED

(71) Applicant: UOP LLC, Des Plaines, IL (US)

(72) Inventors: Paul T. Barger, Arlington Heights, IL (US); Maureen L. Bricker, Buffalo Grove, IL (US); Joseph A. Kocal, Buffalo Grove, IL (US); Matthew Lippmann, Chicago, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,140

(22) Filed: Aug. 26, 2014

(65) Prior Publication Data

US 2015/0141699 A1 May 21, 2015

Related U.S. Application Data

(60) Provisional application No. 61/905,973, filed on Nov. 19, 2013.

(51) Int. Cl.

| C07C 45/53 | (2006.01) |
|---|---|
| C07C 37/08 | (2006.01) |
| C07C 2/00 | (2006.01) |
| C07C 45/50 | (2006.01) |
| C07C 2/70 | (2006.01) |
| C07C 7/00 | (2006.01) |
| C07C 45/45 | (2006.01) |

(52) U.S. Cl.
CPC ............ *C07C 45/505* (2013.01); *C07C 2/70* (2013.01); *C07C 7/00* (2013.01); *C07C 45/45* (2013.01); *C07C 45/455* (2013.01); *C07C 2531/04* (2013.01)

(58) Field of Classification Search
CPC ............ C07C 45/53; C07C 37/08; C07C 2/66
USPC .......................... 568/397, 768; 585/323, 446
See application file for complete search history.

(56) References Cited

U.S. PATENT DOCUMENTS

| 3,331,766 A | 7/1967 | Young |
|---|---|---|
| 3,736,250 A | 5/1973 | Berg et al. |
| 3,929,618 A | 12/1975 | Abiko et al. |
| 4,234,408 A | 11/1980 | Duncan |
| 4,305,808 A | 12/1981 | Bowes et al. |
| 4,608,153 A | 8/1986 | Hudson et al. |
| 4,618,412 A | 10/1986 | Hudson et al. |
| 4,645,585 A | 2/1987 | White |
| 4,921,595 A | 5/1990 | Gruia |
| 4,931,165 A | 6/1990 | Kalnes |
| 4,943,365 A | 7/1990 | Boenigk et al. |
| 5,007,998 A | 4/1991 | Gruia |
| 5,139,644 A | 8/1992 | Gruia |
| 5,266,184 A | 11/1993 | Roder |
| 6,291,724 B1 | 9/2001 | Braat |
| 2011/0270005 A1 | 11/2011 | Yanagawa et al. |
| 2012/0279902 A1 | 11/2012 | McGrady et al. |
| 2013/0006027 A1 | 1/2013 | Yanagawa et al. |
| 2013/0172639 A1 | 7/2013 | Yanagawa et al. |
| 2013/0178673 A1 | 7/2013 | Kim et al. |
| 2013/0184506 A1 | 7/2013 | Yanagawa et al. |

FOREIGN PATENT DOCUMENTS

| CN | 101643654 A | 2/2010 |
|---|---|---|
| CN | 102181299 A | 9/2011 |
| EP | 2630106 | 4/2012 |
| GB | 1232027 | 5/1971 |
| JP | 6200254 A2 | 7/1994 |
| KR | 2012077973 A | 7/2012 |
| KR | 2012078006 A | 7/2012 |
| KR | 2012078032 A | 7/2012 |
| WO | WO 2012/133197 A1 | 3/2012 |
| WO | WO 2012/053848 A3 | 4/2012 |
| WO | WO 2012/070706 A1 | 5/2012 |
| WO | WO 2012/133138 A1 | 10/2012 |
| WO | WO 2012/133168 A1 | 10/2012 |
| WO | WO 2012/161264 A1 | 11/2012 |
| WO | WO 2012/161281 A1 | 11/2012 |

OTHER PUBLICATIONS

Stephens et al., "The kinetics of catalytic hydrogenation of pyrene . . . ," American Chemical Society, Sandia National Laboratories (1983), 28(5), 161-168.
Gore et al., "Studies in the Acylation of Anthracene," Journal of the Chemical Society (1964), vol. 1, 5666-5674.
Search Report dated Feb. 9, 2015 for corresponding PCT Appl. No. PCT/US2014/061877.

*Primary Examiner* — Sikarl Witherspoon

(57) ABSTRACT

A process for pyrolyzing a coal feed is described. A coal feed is pyrolyzed into a coal tar stream and a coke stream in a pyrolysis zone. The coal tar stream is separated into at least a pitch stream comprising aromatic hydrocarbons. The pitch stream is reacted in a reaction zone to add at least one functional group to an aromatic ring of the aromatic hydrocarbons in the pitch stream. The functionalized pitch stream is recycled to the pyrolysis zone.

19 Claims, 1 Drawing Sheet

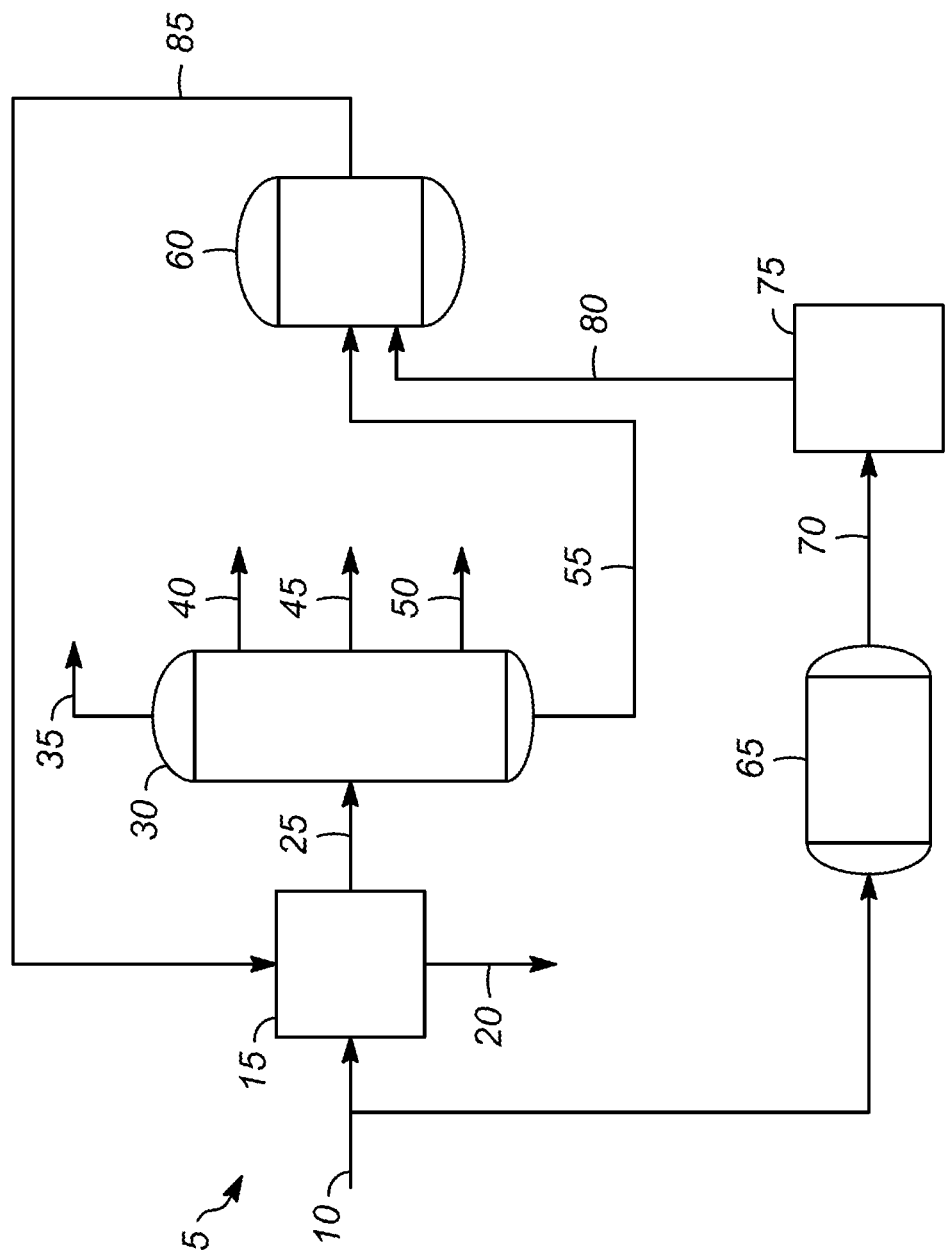

PROCESS FOR PYROLYSIS OF A COAL FEED

This application claims the benefit of Provisional Application Ser. No. 61/905,973 filed Nov. 19, 2013, entitled Process for Pyrolysis of a Coal Feed.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which is used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains.

While lighter hydrocarbon streams from coal tar can be more easily processed to produce desirable products, the pitch stream includes aromatic cores that make the pitch more difficult to react in further processing. The residual pitch left from the separation conventionally is used for paving, roofing, waterproofing, and insulation.

There is a need for improved processes for pyrolyzing a coal feed.

SUMMARY OF THE INVENTION

One aspect of the invention involves a process for pyrolyzing a coal feed. A coal feed is pyrolyzed into a coal tar stream and a coke stream in a pyrolysis zone. The coal tar stream is separated into at least a pitch stream comprising aromatic hydrocarbons. The pitch stream is reacted in a reaction zone to add at least one functional group to an aromatic ring of the aromatic hydrocarbons in the pitch stream. The functionalized pitch stream is recycled to the pyrolysis zone.

Another aspect of the invention involves a process for pyrolyzing a coal feed. A first coal feed is pyrolyzed into a coal tar stream and a coke stream in a pyrolysis zone. The coal tar stream is separated into at least a pitch stream comprising aromatic hydrocarbons. A second coal feed is gasified to produce a syngas stream comprising $H_2$ and CO. The syngas stream is processed to produce one or more of methanol, olefins, acetic acid, and formic acid. The one or more of methanol, olefins, acetic acid, and formic acid is fed to a reaction zone. The pitch stream is reacted in the reaction zone to add at least one functional group to an aromatic ring of the aromatic hydrocarbons in the pitch stream. The functionalized pitch stream is recycled into the pyrolysis zone.

BRIEF DESCRIPTION OF THE DRAWING

The FIGURE is an illustration of one embodiment of the process of the present invention.

DETAILED DESCRIPTION OF THE INVENTION

The FIGURE shows one embodiment of a coal conversion process 5. The coal feed 10 can be sent to a pyrolysis zone 15 or a gasification zone 65, or the coal feed 10 can be split into two parts and sent to both.

In the pyrolysis zone 15, the coal feed 10 is heated at high temperature, e.g., up to about 2,000° C. (3600° F.), in the absence of oxygen to drive off the volatile components. Pyrolyzing the coal feed 10 produces a coke stream 20 and a coal tar stream 25. The coke stream 20 can be used in other processes, such as the manufacture of steel.

In the gasification zone 65, all or a portion of the coal feed 10 is mixed with oxygen and steam and reacted under heat and pressure in the gasification zone 65 to form a syngas stream 70. The syngas stream 70 is a mixture of carbon monoxide and hydrogen.

The coal tar stream 25 is sent to a separation zone 30 where it is separated into at least a pitch stream. Preferably, the coal tar stream 25 is separated into two or more fractions. Suitable separation processes include, but are not limited to fractionation, solvent extraction, and adsorption. Coal tar comprises a complex mixture of heterocyclic aromatic compounds and their derivatives with a wide range of boiling points. The number of fractions and the components in the various fractions can be varied as is well known in the art. A typical separation process involves separating the coal tar stream 25 into four to six streams. For example, there can be a fraction 35 comprising $NH_3$, CO, and light hydrocarbons, a light oil fraction 40 with boiling points between 0° C. and 180° C., a middle oil fraction 45 with boiling points between 180° C. to 230° C., a heavy oil fraction 50 with boiling points between 230 to 270° C., an anthracene oil fraction (not shown) with boiling points between 270° C. to 350° C., and a pitch stream 55.

The light oil fraction 40 contains compounds such as benzenes, toluenes, xylenes, naphtha, coumarone-indene, dicyclopentadiene, pyridine, and picolines. The middle oil fraction 45 contains compounds such as phenols, cresols and cresylic acids, xylenols, naphthalene, high boiling tar acids, and high boiling tar bases. The heavy oil fraction 50 contains creosotes. The anthracene oil fraction (not shown) contains anthracene. The pitch stream 55 is the residue of the coal tar distillation containing primarily aromatic hydrocarbons and heterocyclic compounds.

The pitch stream 55 includes aromatic hydrocarbons such as polynuclear aromatic (PNA) cores that are difficult to react for further processing, as compared to lighter hydrocarbon fractions. In the process 5, this pitch stream 55 is sent to a reaction zone 60 for functionalizing the pitch stream 55. In the reaction zone 60, at least one functional group is added to an aromatic ring of the aromatic hydrocarbons in the pitch stream 55. This functionalizes the aromatic cores in the pitch stream 55 to make then more reactive; for instance, the functionalized aromatic cores can crack open more easily in a subsequent thermal reaction. Typical functionalization involves alkylation (e.g., methylation), acylation, and formylation.

The functionalized pitch stream 85 from the reaction zone 60 is recycled to the pyrolysis zone 15. Additional coal feed 10 can also be fed to the pyrolysis zone 15. For example, the functionalized pitch stream 85 can be combined with the new coal feed 10, and this combined feed can be fed to the pyrolysis zone 15, or the functionalized pitch stream and new coal feed can be delivered to the pyrolysis zone separately.

The reaction zone 60 preferably is selected from the group consisting of a fixed bed reactor, a slurry reactor, a fluidized bed reactor, an ebulating bed reactor, a transport bed reactor, a two-phase bed reactor, a riser reactor, and a batch reactor. The type of reactor can vary depending on the particular reaction employed. In the reaction zone 60, the pitch stream is contacted with an acid catalyst, which can be a solid catalyst or a liquid acid catalyst.

Example liquid acid catalysts include a liquid acid selected from the group consisting of hydrofluoric acid, sulfuric acid, HCl, acetic acid, formic acid, and sulfuric acid. Example solid catalysts include catalysts selected from the group consisting of metal oxides such as alumina, mixed metal oxides such as silica-alumina and tungstated zirconia, metal halides such as $AlCl_3$, $TiCl_4$, $CuCl_2$ and $BF_3$, modified metal oxides such as sulfated zirconia, and $AlCl_3$-treated alumina, zeolites, non-zeolitic molecular sieves, clays and sulfonic acid resins.

In the process 5, the syngas stream 70 from the gasification zone 65 includes $H_2$ and CO. This syngas stream 70 can be processed, e.g., reacted in a syngas reaction zone 75 over a suitable catalyst to produce compounds which can be used to functionalize the pitch stream 55. This feedstream 80 can then be fed to the reaction zone 60.

In an alternative embodiment, the feedstream 80 can be supplied from an alternative source that is not prepared from syngas made by coal gasification.

Alkylating the pitch stream 55 can include, for example, contacting the pitch stream 55 with at least one of an olefin, an alcohol or an alkyl halide and a catalyst selected from the group consisting of solid and liquid acids, including metal oxides such as alumina, mixed metal oxides such as silica-alumina and tungstated zirconia, metal halides such as $AlC_3$, $TiCl_4$, $CuCl_2$ and $BF_3$, modified metal oxides such as sulfated zirconia, and $AlCl_3$-treated alumina, zeolites, non-zeolitic molecular sieves, clays, sulfonic acid resins, HF, HCl and $H_2SO_4$. Reaction conditions include a temperature between about 50° C. and about 300° C. and a pressure between about 345 kPa (50 psig) and about 6.89 MPa (1,000 psig). The syngas stream 70 can be reacted in the syngas reaction zone 75 over a catalyst such as Cu/ZnO, alkali-modified Cu/ZnO and supported $MoS_2$, $Mo_2C$ or Rh supported on $Al_2O_3$ or $SiO_2$ at reaction conditions including a temperature between about 150° C. and about 350° C., and a pressure between about 1.38 MPa (200 psig) and about 13.8 MPa (2000 psig) to produce an alcohol. The alcohol can be reacted with the pitch stream 55. Alternatively, the alcohol can be converted to olefins in an olefin production zone, which can be part of the syngas reaction zone 75 or a separate zone, under reaction conditions such as a temperature between about 25° C. and about 250° C. and a pressure between about 345 kPa (50 psig) and about 6.89 MPa (1,000 psig) using a catalyst such as alumina, zeolites, amorphous $SiO_2$—$Al_2O_3$ and sulfonic acid resins to produce olefins for the feedstream 80. Example olefins that may be produced include ethylene, propylene, and butenes.

For example, methylating the pitch stream 55 can include contacting the pitch stream 55 with methanol or a methyl halide and a catalyst selected from the group consisting of solid and liquid acids, including metal oxides such as alumina, mixed metal oxides such as silica-alumina and tungstated zirconia, metal halides such as $AlCl_3$, $TiCl_4$ and $BF_3$, modified metal oxides such as sulfated zirconia, and $AlCl_3$-treated alumina, zeolites, non-zeolitic molecular sieves, clays, sulfonic acid resins, HF, HCl and $H_2SO_4$. Reaction conditions include a temperature between about 50° C. and about 300° C. and a pressure between about 345 kPa (50 psig) and about 6.89 MPa (1,000 psig). To provide methanol for the methylation, the syngas stream 70 can be reacted in the syngas reaction zone 75 over a catalyst such as Cu/ZnO at reaction conditions including a temperature between about 50° C. and about 300° C. and a pressure between about 345 kPa (50 psig) and about 6.89 MPa (1,000 psig) to produce methanol in the feedstream 80.

Acylating the pitch stream 55 can include, for example, contacting the pitch stream 55 with acetic acid, acetyl chloride or acetic anhydride and a catalyst selected from the group consisting of solid and liquid acids, including metal oxides such as alumina, mixed metal oxides such as silica-alumina and tungstated zirconia, metal halides such as $AlCl_3$, $TiCl_4$, $CuCl_2$ and $BF_3$, modified metal oxides such as sulfated zirconia, and $AlCl_3$-treated alumina, zeolites, non-zeolitic molecular sieves, clays, sulfonic acid resins, HF, HCl and $H_2SO_4$. Reaction conditions include a temperature between about 0° C. and about 250° C. and a pressure between about 345 kPa (50 psig) and about 6.89 MPa (1,000 psig). To provide acetic acid for the acylation, the syngas stream 70 can be reacted in the syngas reaction zone 75 over a catalyst such as Cu/ZnO at reaction conditions including a temperature between about 50° C. and about 300° C. and a pressure between about 345 kPa (50 psig) and about 6.89 MPa (1,000 psig) to produce methanol which can then be reacted with additional CO over a catalyst such as homogeneous Rh or Ir at reaction conditions including a temperature between about 150° C. and about 250° C. and a pressure between about 2070 kPa (300 psig) and about 6.89 MPa (1,000 psig) to produce acetic acid in the feedstream 80.

Formylating the pitch stream 55 can include, for example, contacting the pitch stream 55 with a formylating agent, comprising formic acid, formaldehyde, dimethylformamide, CO and dichloromethylmethyl ether, and a catalyst selected from the group consisting of solid and liquid acids, including metal oxides such as alumina, mixed metal oxides such as silica-alumina and tungstated zirconia, metal halides such as $AlCl_3$, $TiC_4$ and $BF_3$, modified metal oxides such as sulfated zirconia, and $AlO_3$-treated alumina, zeolites, non-zeolitic molecular sieves, clays, sulfonic acid resins, $POCl_3$, HF, HCl and $H_2SO_4$. To provide formic acid for the formylation, the syngas stream 70 can be reacted over a catalyst such as Cu/ZnO at reaction conditions including a temperature between about 50° C. and about 300° C. and a pressure between about 345 kPa (50 psig) and about 6.89 MPa (1,000 psig) to produce methanol which can then be oxidized with $O_2$ over a catalyst such as Ag metal at reaction conditions including a temperature between about 600° C. and about 700° C. to produce formic acid for the feedstream 80. The formic acid can be reacted with the pitch.

Pyrolyzing the recycled functionalized pitch stream 85, alone or with additional coal feed 10, provides a coal tar stream 25 output having lighter fractions. The pyrolysis zone 15, the separation zone 30 and the reaction zone 60, with new coal feed 10 for pyrolysis, can provide a cycle that is repeated multiple times to provide a progressively lighter, more reactive product for additional processing.

One or more of the fractions 35, 40, 45, 50 (hydrocarbon streams) can be recovered as at least one product, or may be further processed as desired to recover at least one product. Suitable hydrocarbon conversion zones include, but are not limited to, hydrotreating zones, hydrocracking zones, fluid catalytic cracking zones, alkylation zones, transalkylation zones, oxidation zones, and hydrogenation zones.

Hydrotreating is a process in which hydrogen gas is contacted with a hydrocarbon stream in the presence of suitable catalysts which are primarily active for the removal of heteroatoms, such as sulfur, nitrogen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 26.7 MPa (4000 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bhp. Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

Hydrocracking is a process in which hydrocarbons crack in the presence of hydrogen to lower molecular weight hydrocarbons. Typical hydrocracking conditions may include a temperature of about 290° C. (550° F.) to about 468° C. (875° F.), a pressure of about 3.5 MPa (500 psig) to about 20.7 MPa (3000 psig), a liquid hourly space velocity (LHSV) of about 1.0 to less than about 2.5 $hr^{-1}$, and a hydrogen rate of about 421 to about 2,527 $Nm^3/m^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base.

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a powdered catalyst having the particles suspended in a rising flow of feed hydrocarbons to twin a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPa g (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutane alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7100 kPa absolute. The temperature range covered by this set of conditions is from about −20° C. to about 200° C. For the alkylation of aromatic compounds over solid acid catalysts, the temperature range is about from 100-200 C at the pressure range of about 200 to about 7100 kPa.

Transalkylation is a chemical reaction resulting in transfer of an alkyl group from one organic compound to another. Catalysts, particularly zeolite catalysts, are often used to effect the reaction. If desired, the transalkylation catalyst may be metal stabilized using a noble metal or base metal, and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream comprising unconverted feed and product monoalkylated hydrocarbons. This effluent is normally cooled and passed to a stripping column in which substantially all C5 and lighter hydrocarbons present in the effluent are concentrated into an overhead stream and removed from the process. An aromatics-rich stream is recovered as net stripper bottoms, which is referred to as the transalkylation effluent.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour; weight hourly space velocity (WHSV) generally is in the range of from about 0.1 to about 30 hr$^{-1}$. The catalyst is typically selected to have relatively high stability at a high activity level.

Oxidation involves the oxidation of hydrocarbons to oxygen-containing compounds, such as alcohols, aldehydes, ketones, carboxylic acids and epoxides. The hydrocarbons include alkanes, alkenes, typically with carbon numbers from 2 to 15, and alkyl aromatics, Linear, branched, and cyclic alkanes and alkenes can be used. Oxygenates that are not fully oxidized to ketones or carboxylic acids can also be subjected to oxidation processes, as well as sulfur compounds that contain —S—H moieties, thiophene rings, and sulfone groups. The process is carried out by placing an oxidation catalyst in a reaction zone and contacting the feed stream which contains the desired hydrocarbons with the catalyst in the presence of oxygen. The type of reactor which can be used is any type well known in the art such as fixed-bed, moving-bed, multi-tube, CSTR, fluidized bed, etc. The feed stream can be flowed over the catalyst bed either up-flow or down-flow in the liquid, vapor, or mixed phase. In the case of a fluidized-bed, the feed stream can be flowed co-current or counter-current. In a CSTR the feed stream can be continuously added or added batch-wise. The feed stream contains the desired oxidizable species along with oxygen. Oxygen can be introduced either as pure oxygen or as air, or as liquid phase oxidents including hydrogen peroxide, organic peroxides, or peroxy-acids. The molar ratio of oxygen ($O_2$) to alkane can range from about 5:1 to about 1:10. In addition to oxygen and alkane or alkene, the feed stream can also contain a diluent gas selected form nitrogen, neon, argon, helium, carbon dioxide, steam or mixtures thereof. As stated, the oxygen can be added as air which could also provide a diluent. The molar ratio of diluent gas to oxygen ranges from greater than zero to about 10:1. The catalyst and feed stream are reacted at oxidation conditions which include a temperature of about 300° C. to about 600° C., a pressure of about 101 kPa to about 5,066 kPa and a gas hourly space velocity of about 100 to about 100,000 hr$^{-1}$.

Hydrogenation involves the addition of hydrogen to hydrogenatable hydrocarbon compounds to provide products with a lower degree of unsaturation, such as paraffins and naphthenes. The hydrogenatable hydrocarbon compounds are introduced into a hydrogenation zone and contacted with a hydrogen-rich gaseous phase and a hydrogenation catalyst in order to hydrogenate at least a portion of the hydrogenatable hydrocarbon compounds. Alternatively, a hydrogenation process can be provided in which a hydrogen-containing compound with readily available hydrogen, such as tetralin, alcohols, hydrogenated naphthalenes, and others provides hydrogen via a transfer hydrogenation process with or without a catalyst. The catalytic hydrogenation zone may contain a fixed, ebulated or fluidized catalyst bed. This reaction zone is typically at a pressure from about 689 k Pa gauge (100 psig) to about 13790 k Pa gauge (2000 psig) with a maximum catalyst bed temperature in the range of about 177° C. (350° F.) to about 454° C. (850° F.). The liquid hourly space velocity is typically in the range from about 0.2 hr$^{-1}$ to about 10 hr$^{-1}$ and hydrogen circulation rates from about 200 standard cubic feet per barrel (SCFB) (35.6 m$^3$/m$^3$) to about 10,000 SCFB (1778 m$^3$/m$^3$).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process comprising:
   pyrolyzing a coal feed into a coal tar stream and a coke stream in a pyrolysis zone;
   fractionating the coal tar stream into at least a pitch stream comprising aromatic hydrocarbons;
   reacting the pitch stream in a reaction zone to add at least one functional group to an aromatic ring of the aromatic hydrocarbons in the pitch stream; and
   recycling the functionalized pitch stream to the pyrolysis zone.

2. The process of claim 1 wherein reacting the pitch stream comprises one or more of alkylating the pitch stream, methylating the pitch stream, acylating the pitch stream, and formylating the pitch stream.

3. The process of claim 1 wherein the reaction zone is selected from the group consisting of a fixed bed reactor, a slurry reactor, a fluidized bed reactor, an ebulating bed reactor, a transport bed reactor, a two-phase bed reactor, a riser reactor, and a batch reactor.

4. The process of claim 1 wherein reacting the pitch stream comprises contacting the pitch stream with an acid catalyst.

5. The process of claim 1 wherein reacting the pitch stream further comprises feeding at least one of an olefin and an alcohol into the reaction zone.

6. The process of claim 1 wherein reacting the pitch stream comprises methylating the pitch stream.

7. The process of claim 6 wherein methylating the pitch stream comprises contacting the pitch stream with methanol or a methyl halide and a catalyst selected from the group consisting of metal oxides, mixed metal oxides, metal halides, modified metal oxides, zeolites, non-zeolitic molecular sieves, clays, sulfonic acid resins, HF, HCl and $H_2SO_4$.

8. The process of claim 6 further comprising:
   gasifying a portion of the coal feed to produce a syngas stream comprising $H_2$ and CO;
   reacting the syngas stream over a catalyst to produce methanol; and
   feeding the methanol to the reaction zone.

9. The process of claim 1 wherein reacting the pitch stream comprises acylating the pitch stream.

10. The process of claim 9 wherein acylating the pitch stream comprises contacting the pitch stream with acetic acid, acetyl chloride or acetic anhydride and a catalyst selected from the group consisting of metal oxides, mixed metal oxides, metal halides, modified metal oxides, zeolites, non-zeolitic molecular sieves, clays, sulfonic acid resins, HF, HCl and $H_2SO_4$.

11. The process of claim 10 further comprising:
   gasifying a portion of the coal feed to produce a syngas stream comprising $H_2$ and CO;
   reacting the syngas stream over a catalyst to produce acetic acid; and
   feeding the acetic acid to the reaction zone.

12. The process of claim 1 wherein reacting the pitch stream comprises alkylating the pitch stream.

13. The process of claim 12 wherein alkylating the pitch stream comprises contacting the pitch stream with at least one of an olefin, an alcohol or an alkyl halide and a catalyst selected from the group consisting of metal oxides, mixed metal oxides, metal halides, modified metal oxides, zeolites, non-zeolitic molecular sieves, clays, sulfonic acid resins, HF, HCl and $H_2SO_4$.

14. The process of claim 13 further comprising:
gasifying a portion of the coal feed to produce a syngas stream comprising $H_2$ and CO;
processing the syngas stream to produce methanol;
converting the alcohol to olefins; and
feeding the olefins to the reaction zone.

15. The process of claim 1 wherein reacting the pitch stream comprises formylating the pitch stream.

16. The process of claim 15 wherein formylating the pitch stream comprises contacting the pitch stream with a formylating agent, comprising formic acid, formaldehyde, dimethylformamide, CO and dichloromethylmethyl ether, and a catalyst selected from the group consisting of metal oxides, mixed metal oxides, metal halides, modified metal oxides, zeolites, non-zeolitic molecular sieves, clays, sulfonic acid resins, $POCl_3$, HF, HCl and $H_2SO_4$.

17. The process of claim 15 further comprising:
gasifying a portion of the coal feed to produce a syngas stream comprising $H_2$ and CO;
reacting the syngas stream over a catalyst to produce formic acid; and
feeding the formic acid to the reaction zone.

18. The process of claim 15 further comprising:
gasifying a portion of the coal feed to produce a syngas stream comprising $H_2$ and CO; and
feeding the CO to the reaction zone.

19. A process comprising:
pyrolyzing a first coal feed into a coal tar stream and a coke stream in a pyrolysis zone;
fractionating the coal tar stream into at least a pitch stream comprising aromatic hydrocarbons;
gasifying a second coal feed to produce a syngas stream comprising $H_2$ and CO;
processing the syngas stream to produce one or more of methanol, olefins, acetic acid, and formic acid;
feeding the one or more of methanol, olefins, acetic acid, and formic acid into a reaction zone;
reacting the pitch stream in the reaction zone to add at least one functional group to an aromatic ring of the aromatic hydrocarbons in the pitch stream; and
recycling the functionalized pitch stream into the pyrolysis zone.

\* \* \* \* \*